United States Patent
Jäverud et al.

(10) Patent No.: US 7,089,051 B2
(45) Date of Patent: Aug. 8, 2006

(54) IMPLANTABLE MEDICAL DEVICE WITH VALVE OPENING DETECTOR

(75) Inventors: Karin Jäverud, Solna (SE); Kjell Norén, Solna (SE)

(73) Assignee: St. Jude Medical AB, Jarfalla (SE)

(*) Notice: Subject to any disclaimer, the term of this patent is extended or adjusted under 35 U.S.C. 154(b) by 462 days.

(21) Appl. No.: 10/311,616

(22) PCT Filed: Jun. 19, 2001

(86) PCT No.: PCT/SE01/01424

§ 371 (c)(1),
(2), (4) Date: Dec. 17, 2002

(87) PCT Pub. No.: WO02/00296

PCT Pub. Date: Jan. 3, 2002

(65) Prior Publication Data

US 2003/0181952 A1 Sep. 25, 2003

(30) Foreign Application Priority Data

Jun. 30, 2000 (SE) .................................. 0002514

(51) Int. Cl.
*A61B 5/053* (2006.01)
(52) U.S. Cl. ..................................................... 600/547
(58) Field of Classification Search .................. 600/547
See application file for complete search history.

(56) References Cited

U.S. PATENT DOCUMENTS

| | | | |
|---|---|---|---|
| 4,730,619 A | 3/1988 | Koning et al. | |
| 5,129,394 A | 7/1992 | Mehra | |
| 5,454,838 A * | 10/1995 | Vallana et al. | ................. 607/19 |
| 5,735,883 A | 4/1998 | Paul et al. | |
| 5,792,194 A | 8/1998 | Morra | |
| 5,902,325 A | 5/1999 | Condie et al. | |
| 5,954,752 A | 9/1999 | Mongeon et al. | |
| 5,995,870 A | 11/1999 | Cazeau et al. | |
| 6,070,100 A * | 5/2000 | Bakels et al. | ................... 607/9 |

* cited by examiner

*Primary Examiner*—Robert E. Pezzuto
*Assistant Examiner*—Kristen Mullen
(74) *Attorney, Agent, or Firm*—Schiff Hardin LLP

(57) ABSTRACT

A valve opening detector for use in an implantable medical device detects opening of at least one valve in the left side of heart, and has an impedance measuring unit for measuring electrical impedance between measuring poles and for generating an impedance signal corresponding thereto, at least one of the poles being arranged in the coronary sinus and/or in the great cardiac vein of the heart. The valve opening detector also includes an impedance signal processor which processes the impedance signal to detect the opening of one or both valves in the left side of the heart.

17 Claims, 5 Drawing Sheets

FIG. 1a
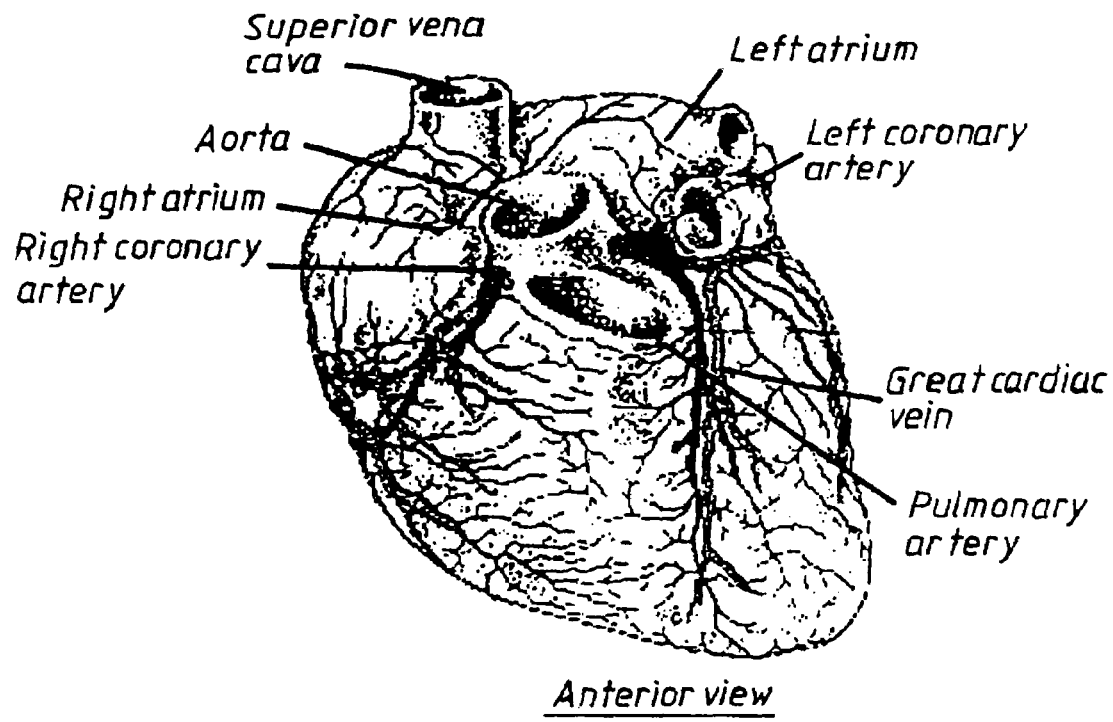
Anterior view
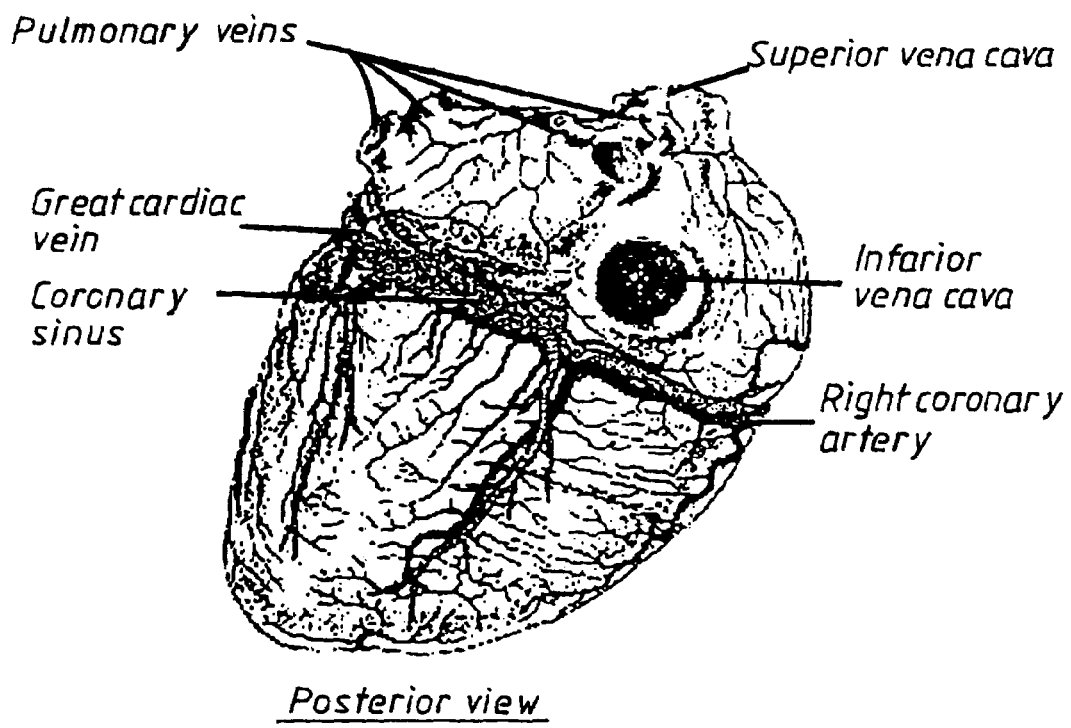
Posterior view
FIG. 1b

FIG. 3a
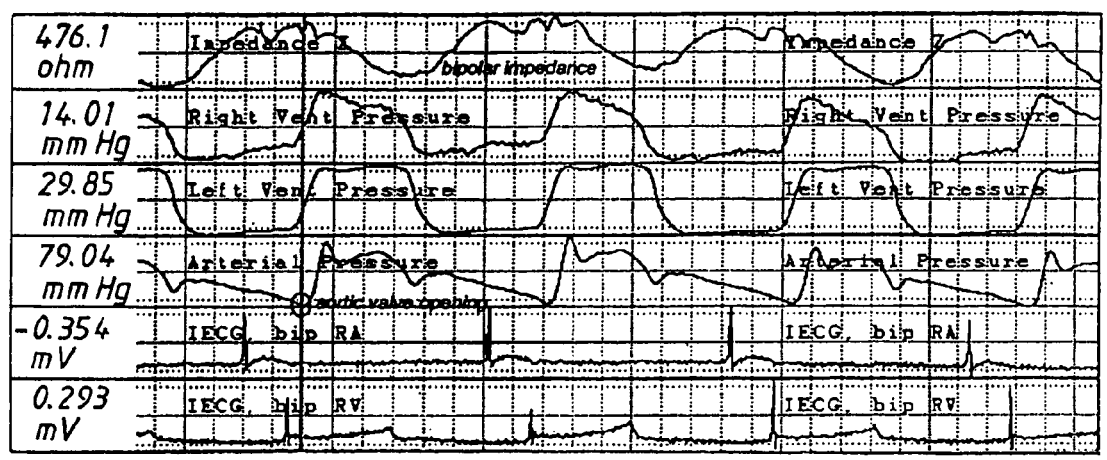
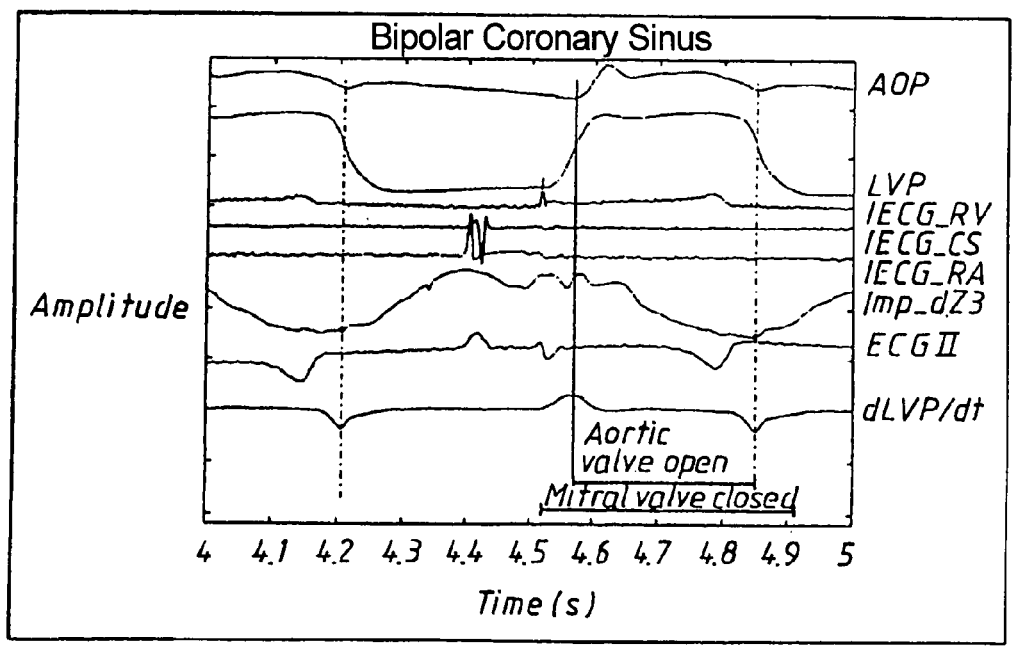
FIG. 3b

FIG. 4a
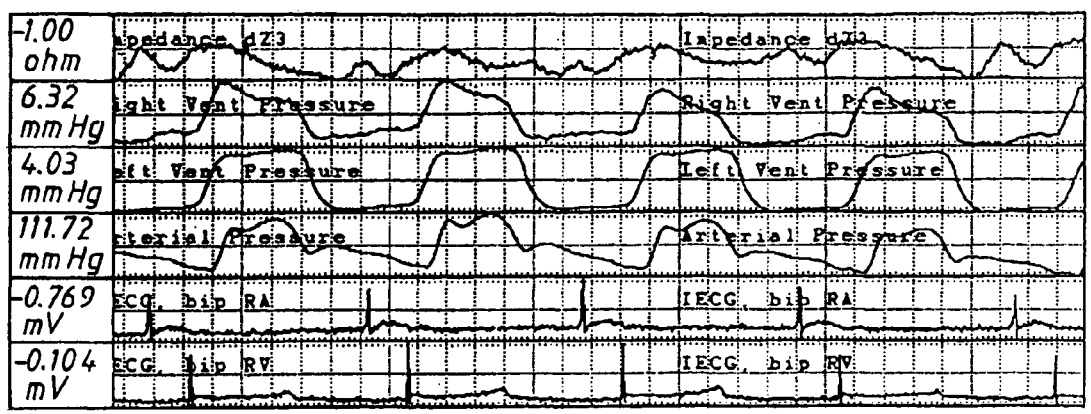
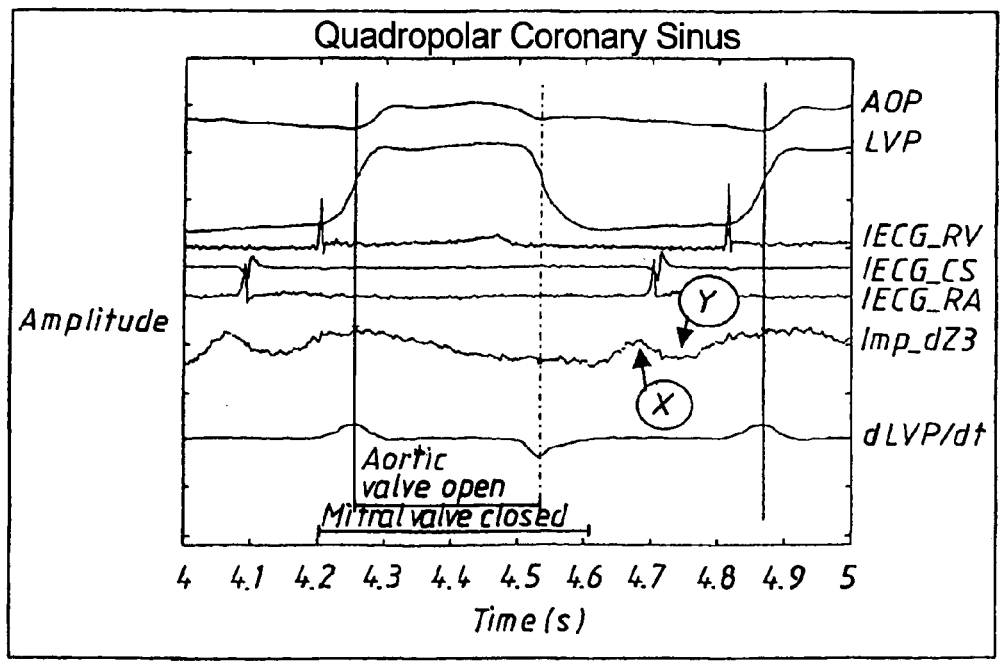
FIG. 4b

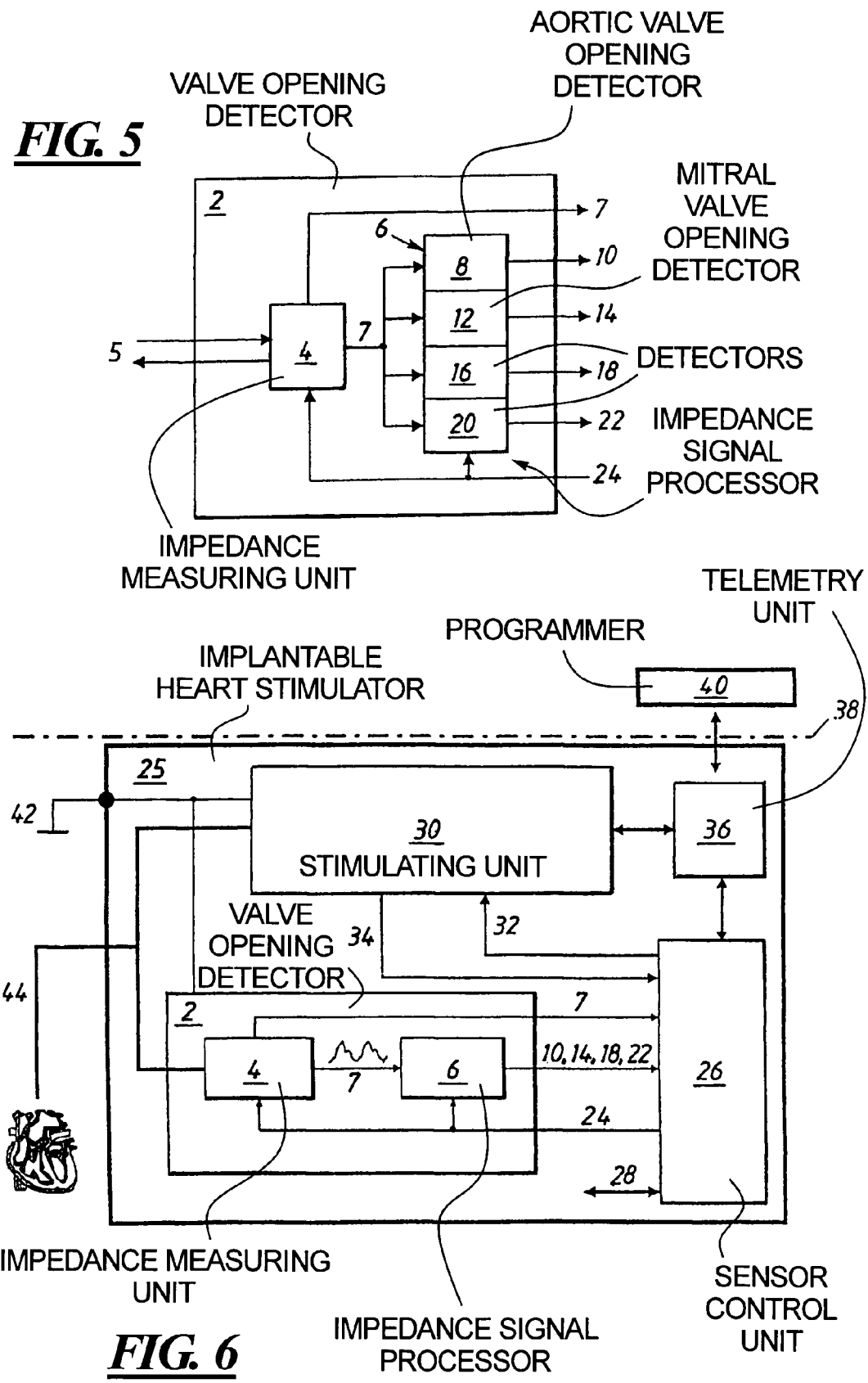

IMPLANTABLE MEDICAL DEVICE WITH VALVE OPENING DETECTOR

BACKGROUND OF THE INVENTION

1. Field of the Invention

The present invention relates to an implantable medical device of the type having a valve opening detector for detecting opening of a valve at the left side of the heart.

2. Description of the Prior Art

Impedance measurements for detection of the flow mechanical function of a heart are known in the art.

In U.S. Pat. No. 5,792,194 a transvalvular impedance measurement is disclosed. The measurement is made between an atrium and a ventricle electrode of an implanted electro-catheter to provide information indicative of the mechanical state of the heart. The information may be used to control the pacing rate of a rate responsive pacemaker, or the stimulation intensity self adjustment or the pacing mode switching. The maximum measured impedance is indicative of the tricuspid valve (the valve between the right atrium and the right ventricle) being closed and the minimum measured impedance is indicative of the tricuspid valve being open. In the device disclosed in U.S. Pat. No. 5,792,194 a signal generator generates a square wave of frequency 4 kHz, amplitude 3 volts. A voltage level is detected at one of the electrodes inside the heart and the detected signal is amplified in an amplifier having a gain in region 50 to 200 and filtered in a filter network. The filter network uses a notch filter to reject mains frequency (50 or 60 Hz) and also a low pass filter to reject frequencies exceeding 100 Hz, since the frequencies of the signals of interest being well below that level. In that way noise generated in impedance measurement can be reduced.

Impedance measurement using four poles is disclosed in U.S. Pat. No. 4,730,619 wherein an electrode lead adapted to be inserted into a heart is provided with a first and a second ring electrode and a tip electrode. A measurement current at any one of several frequencies is applied between the pacer can and the tip electrode and the voltage measured between the ring electrodes is proportional to impedance. The measured impedance is used to determine changes in volume of blood in the right ventricle and to determine opening and closing of the pulmonary valve to determine ejection time. The pulmonary valve is the valve between the right ventricle and the pulmonary artery.

Impedance measurements within a heart may be used to confirm capture, i.e. to confirm that a stimulation pulse applied to heart tissue has caused a heart contraction. U.S. Pat. Nos. 5,737,883 and 5,902,325 both relate to implantable cardiac stimulators provided with capture detection based upon impedance measurements.

Through impedance measurements, blood volume changes are detectable within the area of measurement. Blood has higher conductivity (lower impedance) than myocardial tissue and lungs. The impedance-volume relationship is inverse; the more blood—the smaller the impedance.

In a well functioning heart the left side and the right side of the heart contract more or less simultaneously starting with the contraction of the atria flushing down the blood through the valves separating the atria from the ventricles. In the right side of the heart through the tricuspid valve and in the left side of the heart through the mitral valve. Shortly after the atria contraction the ventricles contract resulting in increasing blood pressure inside the ventricles that first closes the one way valves to the atria and after that forces the outflow valves to open. In the right side of the heart it is the pulmonary valve, that separates the right ventricle from the pulmonary artery that leads blood to the lung to be oxygenated, which is opened. The right side of the heart is termed the low pressure side of the heart since the pressure is several times lower than the pressure in the left side of the heart-termed the high pressure side. In the left side of the heart the aortic valve separates the left ventricle from the aorta that transports blood to the whole body. The outflow valves, the pulmonary valve and the aortic valve, open when the pressure inside the ventricles exceeds the pressure in the pulmonary artery and the aorta, respectively. The ventricles are separated by the intraventricular elastic septum.

The heart is supplied with blood via the left and right coronary arteries having openings close to the aortic valve. The venous blood is returned to the right atrium by the great cardiac vein to the coronary sinus having its opening close to the inferior vena cava.

The measurement device disclosed in U.S. Pat. No. 5,792,194 is adapted to perform measurements in the right side of the heart, the low pressure side of the heart. There is a great interest in making measurements reflecting the hemodynamic of the left side of the heart in order to increase the possibilities to correctly analyze the function of the heart.

SUMMARY OF THE INVENTION

An object of the present invention is to provide a medical device adapted to detect the opening of the valve or valves of the left side of the heart.

The present invention is based on the recognition that the opening of valves in the left side of the heart may be detected by measuring the electrical impedance using at least one measurement pole placed in the coronary sinus or in the great cardiac vein and by performing a tailored processing of the detected impedance signal.

The above object is achieved in accordance with the principles of the present invention in a valve opening detector for use in an implantable medical device, such as an implantable heart stimulator, for detecting the opening of one or more valves in the left side of a heart, wherein the valve opening detector includes an impedance measuring unit for measuring electrical impedance between measurement poles and for generating an impedance signal corresponding thereto, at least one of the poles being arranged in the coronary sinus and/or in the great cardiac vein of the heart, and wherein the valve opening detector further includes an impedance signal processor for processing the impedance signal to detect the opening of one or both valves in the left side of the heart.

In a preferred embodiment the detected valve opening, especially the aortic valve opening, is used as an indication of capture in a stimulation threshold search algorithm in an implantable heart stimulator.

DESCRIPTION OF THE DRAWINGS

FIG. 1a is an anterior view (above) of a human heart, and FIG. 1b is a posterior view (below) of a human heart.

FIGS. 3a and 3b are tracings of an impedance signal obtained by bipolar impedance measurement in accordance with the invention, and other measured signals.

FIGS. 4a and 4b are tracings of an impedance signal obtained by quadropolar impedance measurement in accordance with the invention, and other measured signals.

FIG. 5 is a block diagram of a valve opening detector constructed and operating in accordance with the principles of the present invention.

FIG. 6 is a block diagram of an implantable heart stimulator incorporating a valve opening detector, in accordance with the principles of the present invention.

DESCRIPTION OF THE PREFERRED EMBODIMENTS

FIG. 1a shows an anterior view and FIG. 1b shows a posterior view of a human heart. A simplified description of the coronary vessels is as follows. The right and left coronary arteries supply the heart tissue with arterial blood. As can be seen from the anterior view they are supplied with blood via openings close to aorta. The venous blood is returned into the right atrium via the great cardiac vein and coronary sinus that has its outflow close to the interior vena cava. The coronary sinus essentially follows the horizontal plane of the valves separating the atria from the ventricles. Also the first part of the great cardiac vein follows the horizontal plane a short distance before it turns down towards apex.

By arranging an electrode lead provided with stimulation electrodes and/or sensing means within coronary sinus or great cardiac vein sensing and stimulation of the left side of the heart is possible. This is a well-known technique and is described, for example, in U.S. Pat. No. 5,129,394 that discloses a method and apparatus for controlling heart rate in proportion to left ventricular pressure. A lead with a pressure sensor near its distal end is placed transvenously through the coronary sinus and located in the coronary vein. The pressure that is sensed in that location is proportional to the left ventricular pressure.

The opening of the aortic valve and the mitral valve is normally soundless in contrast to the closing of the valves that might be detected e.g. by a stethoscope or by any suitable phonographic recording.

As indicated above, when describing related prior art, impedance measurements may be performed by using different numbers of measurement poles.

In a preferred embodiment of the invention a unipolar impedance measurement is performed by positioning one measurement pole in the coronary sinus (CS) or in the great cardiac vein (GCV), abbreviated CS/GCV. The other measurement pole is the indifferent plate (electrode) of the housing of the medical implant. Impedance current is applied between the CS/GCV measurement pole and the indifferent plate (4 kHz square wave having amplitude of 10 µA). A voltage is sensed between the same poles.

Figure 2A:
FIGS. 2a and 2b show tracings of an impedance signal obtained by unipolar impedance measurement in accordance with the invention, together with other measured signals.

FIG. 2a discloses tracings of about four complete heart cycles of an impedance signal (at the top) obtained by unipolar impedance measurement and a number of other measured signals illustrating different heart events in relation to the impedance signal. Below the impedance signal can be seen right and left ventricular pressure obtained by fast response pressure sensor elements of a conventional type. A fluid colon pressure sensor measures the arterial pressure using a sensor element positioned in the aorta. The last two tracings are the bipolar internal electrocardiograms (IECG) in the right atrium (RA) and in the right ventricle (RV), respectively.

The measurement values shown to the left in FIG. 2a are only included to illustrate the magnitudes of the values.

The aortic valve opening is indicated in the aortic pressure tracing and it can easily be identified in the impedance signal as a clear distinct notch.

Figure 2B:
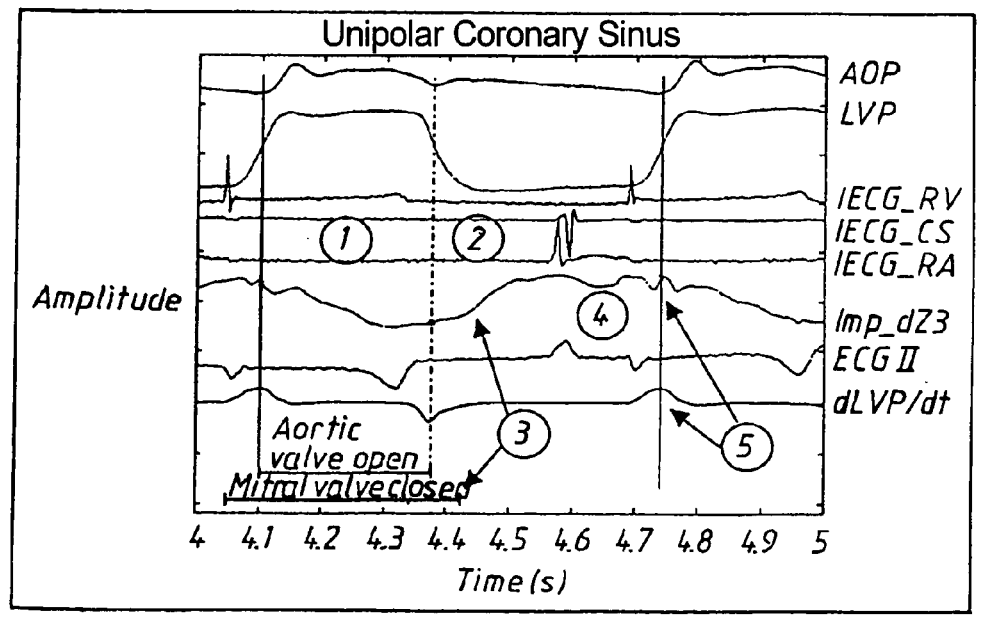

FIG. 2b shows close-up tracings covering a bit more than one heart cycle. From top to bottom is shown the aortic pressure (AOP), the left ventricular pressure (LVP), the internal electrocardiogram in right ventricle, in coronary sinus and in right atrium, respectively (IECG_RV IIECG CS, and IECG_RA respectively), the impedance signal (Imp_dZ3), the external electrocardiogram (ECGII) and the first derivative of left ventricular pressure (dLVP/dt). Different events are identified in FIG. 26 by numbers 1–5.

1. The CS/GCV blood volume is increasing during ventricular systole, which is shown by the decreasing impedance signal.

2. The CS/GCV blood volume is decreasing during early ventricular diastole, which is shown by the increasing impedance signal.

3. The slope of the great cardiac vein impedance signal is slightly changing at mitral valve opening which makes it possible to detect the start of diastole.

4. The CS/GCV blood volume is increasing during atrial systole which is seen as an decreasing impedance signal.

5. The distinct notch in the great cardiac vein blood impedance corresponds to the aortic valve opening.

According to a second preferred embodiment of the invention is bipolar impedance measurement performed by positioning two measurement poles in CS/GCV. Impedance current is applied between the CS/GCV measurement poles (4 kHz square wave having amplitude of 10 µA). A voltage is sensed between the same poles.

FIG. 3a discloses tracings of about four complete heart cycles of an impedance signal (at the top) obtained by bipolar impedance measurement and a number of other measured signals illustrating different heart events in relation to the impedance signal. These other signals correspond to the signals shown in FIG. 2a.

FIG. 3b shows close-up tracings covering a bit more than one heart cycle. The shown tracings correspond to the tracings shown in FIG. 2b.

In another preferred embodiment of the invention a quadropolar impedance measurement is performed by positioning two measurement poles in CS/GCV and using the tip and ring electrodes of a ventricular electrode lead. Impedance current is applied between one of the CS/GCV measurement poles (4 kHz square wave having amplitude of 10 µA) and one of the ventricular electrodes. A voltage is sensed between the other electrodes.

FIG. 4a discloses tracings of about four complete heart cycles of an impedance signal (at the top) obtained by quadropolar impedance measurement and a number of other measured signals illustrating different heart events in relation to the impedance signal. These other signals correspond to the signals shown in FIG. 2a.

FIG. 4b shows close-up tracings covering a bit more than one heart cycle. The shown tracings correspond to the tracings shown in FIG. 2b.

The quadropolar impedance reflects aortic valve opening and the opening of the mitral valve. A change in the impedance signal is seen prior to the atrial contraction (X) possibly indicating a time at which sufficient filling is at hand. The quadropolar impedance decreases at atrial systole (Y), thus enabling hemodynamical atrial capture verification.

FIG. 5 shows a block diagram of the valve opening detector 2 according to the present invention.

The valve opening detector 2 has an impedance measuring unit 4 that perform impedance measurement by applying and receiving impedance measuring signals 5 to and from heart tissue, respectively, e.g. according to the above described technique. The impedance measuring units 4 filters and amplifies the detected impedance signal. The filtered and amplified impedance signal 7 is then applied to an impedance signal processor 6 provided with a number of individual detectors. These detectors are an aortic valve opening detector 8 adapted to generate a first detection signal 10, a mitral valve opening detector 12 adapted to generate a second detection signal 14, a third detector 16 adapted to generate a third detection signal 18 and a forth detector 20 adapted to generate a fourth detection signal 22. Each detector is individually set to identify a specific part of the impedance signal representing a specified heart event. The number of used detectors is naturally optional and depends only on the application.

FIG. 6 shows a block diagram of an implantable heart stimulator 25 provided with a valve opening detector 2 according to the present invention. The heart stimulator 25 has a sensor control unit 26 connected to a heart stimulating unit 30 via connection 32 that provides sensor rate values and timing information to the stimulating unit 30 and also via connection 34 that provides stimulation status and timing information to the sensor control unit 26. The sensor control unit 26 controls the detector 2 via connection 24. The timing information is for instance the detection of a spontaneous QRS or if a stimulation pulse is delivered. The sensor control unit 26 is the interface to the 25 detection signals from the impedance measurement but also to additional sensors connected thereto via connection 28 and additionally, it controls the measurement tuning and weighting of the obtained sensor values. The sensor control unit 26 provides the heart stimulating unit 30 with a sensor rate value that controls the stimulation rate of the pacemaker in dependence of a measured sensor value. This is established technique used in rate responsive pacemakers and therefore need not described any further in the present application.

The sensor control unit 26 and the heart stimulating unit 30 is also connected to a telemetry unit 36 that communicates, preferably via radio-waves, with a programmer 40 placed outside the skin 38 of a patient.

The sensor control unit 26 has a memory wherein preselected events are stored for diagnostic purposes. The memory content can be transferred to the programmer for further analysis. It is also possible to load special algorithms from the programmer into the sensor control unit 26 and heart stimulating unit 30.

FIG. 6 also shows an indifferent electrode 42 which preferably is arranged on the housing of the heart stimulator 25 and an electrode lead 44 that includes at least one electrode lead provided with one or many impedance sensing electrode(s) adapted to be arranged in coronary sinus or in the great cardiac vein. The electrode lead 44 may also include one or many other electrode leads adapted to be arranged in the atrium and/or in the ventricle of the heart.

The aortic valve opening detector 8 includes first impedance signal processor means for processing a detected impedance signal according to a predetermined first signal processing, so that the opening of the aortic valve may be detected. The first signal processing is performed by amplifying and filtering the impedance signal in a first filter having first filter characteristics to filter out the relevant part of the impedance signal, i.e. the sharp notch shown in FIGS. 2–4.

The mitral valve opening detector 12 includes a second impedance signal processor for processing a detected impedance signal according to a predetermined second signal processing. The second signal processing is performed so that the opening of the mitral valve may be detected. The second signal processing is performed by amplifying and filtering the impedance signal in a second filter means having second filter characteristics.

Each of the first and second filter characteristics includes one band-pass filter part with variable lower and upper border frequencies. The lower and upper limit frequencies are set in dependence on the predetermined heart event to be detected. According to a preferred embodiment of the invention the limit frequencies are set for the aortic valve opening detector 10–30 Hz and for the mitral valve opening detector to 2–16 Hz. The filtered signal is then preferably applied to a threshold detector having a, preferably programmable, threshold set in relation to the detected event. The threshold detector may be arranged to be active during a detection window synchronized with a detected QRS-complex or a stimulation pulse. With respect to the aortic valve opening detector the detection window is about 100–200 ms wide (preferably 100 ms), starting immediately after the occurrence of a QRS-complex or the delivery of a stimulation pulse. With respect to the mitral valve opening detector the detection window is about 100–200 ms wide (preferably 100 ms), starting about 200–300 ins. after a detected QRS-complex or the delivery of a stimulation pulse and ending with the next occurrence of a QRS-complex or the next delivery of a stimulation pulse. Preferably, the width of the time windows as well as the starting point in time for the (mitralis valve) window could be dependent on heart rate, such that a higher heart rate is reflected in shorter detection windows and an earlier starting point. The detection of a valve opening could preferably be used for determining, by well-known timer means in the control unit 26, the time interval for the detection within a heart cycle starting from e.g. the occurrence of a QRS-complex or the delivery of a stimulation pulse. This timing information for a valve opening detection can be used e.g. for increased reliability in discrimination between the occurrence of the aortic valve opening and the mitral valve opening, as well as for determining an exact point in time for hemodynamic capture verification (aortic valve opening).

According to a preferred embodiment of the invention at least one impedance measurement pole is adapted to be placed in a cardiac venous vein, e.g. in the coronary sinus or the great cardiac vein. The measurement is then performed between one pole in the cardiac venous vein and an indifferent electrode on the housing of the medical device.

According to another preferred embodiment of the invention the measurement is performed between two poles on an electrode lead adapted to be placed in a cardiac venous vein, e.g. in the coronary sinus or the great cardiac vein.

According to still another embodiment of the invention the measurement is performed between three poles on an electrode lead adapted to be placed in a cardiac venous vein, e.g. in the coronary sinus or the great cardiac vein, and an indifferent electrode on the housing of the medical device.

Although modifications and changes may be suggested by those skilled in the art, it is the invention of the inventors to embody within the patent warranted heron all changes and modifications as reasonably and properly come within the scope of their contribution to the art.

We claim as our invention:

1. An implantable medical device comprising:
    an aortic valve opening detector for detecting opening of the aortic valve of a heart;
    said aortic valve opening detector including an impedance measuring unit for measuring an electrical impedance between measurement poles and generating an impedance signal representing said electrical impedance, at least one of said measurement poles being disposed at a location selected from the group consisting of in the coronary sinus and in the great cardiac vein of said heart; and said aortic valve opening detector further including an impedance signal processor, supplied with said impedance signal, for processing said impedance signal and detecting opening of said aortic valve therefrom.

2. An implantable medical device as claimed in claim 1 wherein said impedance signal processor in said aortic valve opening detector processes said impedance signal according to a predetermined signal processing for detecting said opening of said aortic valve.

3. An implantable medical device as claimed in claim 2 wherein said impedance signal processor comprises a filter having filter characteristics for amplifying and filtering said impedance signal to detect said opening of said aortic valve, as said signal processing.

4. An implantable medical device as claimed in claim 3 wherein said filter has bandpass filter characteristics with a band range of between 10 Hz and 30 Hz.

5. An implantable medical device as claimed in claim 4 wherein said filter has a lower limit frequency and an upper limit frequency defining said band range, each of said upper and lower limit frequencies being variable.

6. An implantable medical device as claimed in claim 1 further comprising a housing containing said valve opening detector, and wherein said impedance measuring unit comprises an electrode lead carrying one pole, and an indifferent electrode on said housing, and wherein said impedance measurement unit measures said electrical impedance between said one pole on said electrode lead and said indifferent electrode.

7. An implantable medical device as claimed in claim 1 further comprising a housing containing said valve opening detector, and wherein said impedance measuring unit comprises an electrode lead carrying two poles, and an indifferent electrode on said housing, and wherein said impedance measurement unit measures said electrical impedance between said two poles on said electrode lead and said indifferent electrode.

8. An implantable medical device as claimed in claim 1 further comprising a housing containing said valve opening detector, and wherein said impedance measuring unit comprises an electrode lead carrying three poles, and an indifferent electrode on said housing, and wherein said impedance measurement unit measures said electrical impedance between said three poles on said electrode lead and said indifferent electrode.

9. An implantable medical device comprising:
a mitral valve opening detector for detecting opening of the mitral valve of a heart;
said mitral valve opening detector including an impedance measuring unit for measuring an electrical impedance between measurement poles and generating an impedance signal representing said electrical impedance, at least one of said measurement poles being disposed at a location selected from the group consisting of in the coronary sinus and in the great cardiac vein of said heart; and
said mitral valve opening detector further including an impedance signal processor, supplied with said impedance signal, for processing said impedance signal by filtering said impedance signal with a filter having bandpass filter characteristics with a band range of between 2 Hz and 16 Hz to detect opening of said mitral valve therefrom.

10. An implantable medical device as claimed in claim 9 wherein said filter has a lower limit frequency and an upper limit frequency defining said band range, said lower and upper limit frequencies being variable.

11. An implantable medical device as claimed in claim 9 wherein said impedance signal processor in said mitral valve opening detector processes said impedance signal according to a predetermined signal processing for detecting said opening of said mitral valve.

12. An implantable heart stimulator comprising:
an aortic valve opening detector for detecting opening of the aortic valve of a heart;
said aortic valve opening detector including an impedance measuring unit for measuring an electrical impedance between measurement poles and generating an impedance signal representing said electrical impedance, at least one of said measurement poles being disposed at a location selected from the group consisting of in the coronary sinus and in the great cardiac vein of said heart;
said aortic valve opening detector further including an impedance signal processor, supplied with said impedance signal, for processing said impedance signal and detecting opening of said aortic valve therefrom;
a stimulation pulse generator for emitting stimulation pulses;
an electrode lead connected to said stimulation pulse generator and adapted for connection to said heart for delivering said stimulation pulses to said heart; and
a control unit connected to said stimulation pulse generator and to said aortic valve opening detector for controlling generation of said stimulation pulses by said stimulation pulse generator dependent on said opening of said aortic valve detected by said aortic valve opening detector.

13. An implantable heart stimulator as claimed in claim 12 wherein said control unit obtains an indication of capture from detection of said opening of said aortic valve by said aortic valve opening detector.

14. An implantable heart stimulator as claimed in claim 12 wherein said control unit controls a timing of said stimulation pulses by said stimulation pulse generator dependent on said detection of said opening of said aortic valve by said aortic valve opening detector.

15. An implantable heart stimulator comprising:
a mitral valve opening detector for detecting opening of the micro valve of a heart;
said mitral valve opening detector including an impedance measuring unit for measuring an electrical impedance between measurement poles and generating an impedance signal representing said electrical impedance, at least one of said measurement poles being disposed at a location selected from the group consisting of in the coronary sinus and in the great cardiac vein of said heart;
said mitral valve opening detector further including an impedance signal processor, supplied with said impedance signal, for processing said impedance signal by filtering said impedance signal with a filter having bandpass filter characteristics with a band range of between 2 Hz and 16 Hz to detect opening of said mitral valve therefrom;
a stimulation pulse generator for emitting stimulation pulses;

an electrode lead connected to said stimulation pulse generator and adapted for connection to said heart for delivering said stimulation pulses to said heart; and a control unit connected to said stimulation pulse generator and to said mitral valve opening detector for controlling generation of said stimulation pulses by said stimulation pulse generator dependent on said opening of said mitral valve detected by said mitral valve opening detector.

16. An implantable heart stimulator as claimed in claim 15 wherein said control unit obtains an indication of capture from detection of said opening of said mitral valve by said mitral valve opening detector.

17. An implantable heart stimulator as claimed in claim 15 wherein said control unit controls a timing of said stimulation pulses by said stimulation pulse generator dependent on said detection of said opening of said mitral valve by said mitral valve opening detector.

* * * * *